(12) United States Patent
Cramer et al.

(10) Patent No.: US 10,888,332 B2
(45) Date of Patent: Jan. 12, 2021

(54) INTRANASAL OCCLUSION DEVICE AND METHODS OF USING THE SAME

(71) Applicant: Northwestern University, Evanston, IL (US)

(72) Inventors: John D. Cramer, Chicago, IL (US); Bruce Kuang-Huay Tan, Chicago, IL (US)

(73) Assignee: NORTHWESTERN UNIVERSITY, Evanston, IL (US)

(*) Notice: Subject to any disclaimer, the term of this patent is extended or adjusted under 35 U.S.C. 154(b) by 78 days.

(21) Appl. No.: 15/618,445

(22) Filed: Jun. 9, 2017

(65) Prior Publication Data

US 2017/0354420 A1     Dec. 14, 2017

Related U.S. Application Data

(60) Provisional application No. 62/349,958, filed on Jun. 14, 2016.

(51) Int. Cl.
| | | |
|---|---|---|
| *A61B 17/12* | (2006.01) | |
| *A61M 1/00* | (2006.01) | |
| *A61M 25/10* | (2013.01) | |
| *A61B 17/24* | (2006.01) | |
| *A61B 17/00* | (2006.01) | |

(52) U.S. Cl.
CPC .... *A61B 17/12136* (2013.01); *A61B 17/1219* (2013.01); *A61B 17/24* (2013.01); *A61B 2017/00898* (2013.01); *A61B 2017/12004* (2013.01); *A61B 2217/005* (2013.01)

(58) Field of Classification Search
CPC .... A61B 17/12136; A61B 2017/12004; A61B 17/12181; A61B 17/1219; A61B 17/24; A61B 2017/00898; A61B 2217/005; A61M 2210/0618; A61M 1/0088
See application file for complete search history.

(56) References Cited

U.S. PATENT DOCUMENTS

| | | | |
|---|---|---|---|
| 3,516,407 | A | 6/1970 | Ruggero |
| 3,884,241 | A | 5/1975 | Walker |
| 4,338,941 | A | 7/1982 | Payton |
| 4,883,465 | A | 11/1989 | Brennan |
| 5,011,474 | A | 4/1991 | Brennan |

(Continued)

FOREIGN PATENT DOCUMENTS

DE     3712502 A1     10/1988

OTHER PUBLICATIONS

Corry J. Kucik, "Management of Epistaxis", American Family Physician, vol. 71, No. 2, pp. 305-311, (2005).

(Continued)

*Primary Examiner* — Manuel A Mendez
*Assistant Examiner* — Justin L Zamory
(74) *Attorney, Agent, or Firm* — Locke Lord LLP; Tim Tingkang Xia, Esq.

(57) ABSTRACT

An intranasal occlusion device having an inflatable balloon within a sponge that is used to prevent drainage of fluid, such as blood and other fluids into the airway during sinus and nasal minor procedures or surgeries, and methods of using the device to occlude an intranasal cavity of a patient. The device provides for suction to remove the fluid and may facilitate office-based minor procedures or surgeries.

20 Claims, 6 Drawing Sheets

(56) References Cited

U.S. PATENT DOCUMENTS

| | | | |
|---|---|---|---|
| 5,827,224 A * | 10/1998 | Shippert | A61B 17/12022 604/73 |
| 7,695,490 B2 | 4/2010 | Hogle | |
| 2015/0148785 A1 * | 5/2015 | Kleiner | A61M 1/0088 604/543 |

OTHER PUBLICATIONS

Brochure, Epistaxis Devices with Rapid Rhino Technology, Smith &Nephew, pp. 1-3.

* cited by examiner

INTRANASAL OCCLUSION DEVICE AND METHODS OF USING THE SAME

CROSS REFERENCE TO RELATED APPLICATION

This application claims the benefit of U.S. Provisional Patent Application Ser. No. 62/349,958, filed Jun. 14, 2016, the disclosure of which is hereby incorporated by reference in its entirety.

FIELD OF THE INVENTION

The disclosure relates to devices and methods used to occlude the choanae and nasopharynx during minor procedures or surgeries, and more particularly to an intranasal occlusion device having an inflatable balloon within a sponge that is used to prevent drainage of blood, other body fluids (e.g., pus, cyst fluid), medications or saline irrigation fluid into the airway during sinus and nasal minor procedures or surgeries and which may be used in an office-based setting.

BACKGROUND

Currently, the vast majority of nasal and sinus surgery is performed in an operating room, with the patient under general anesthesia. Even minor procedures tend to be performed with the expense of general anesthesia, to prevent drainage of blood, or other fluids into the airway and potential aspiration of blood or other fluids. Current techniques for local and intravenous anesthesia enable a variety of minor surgeries to be performed in an office-based setting, however, drainage of blood or other fluids into the upper airway during nasal and sinus surgery risks aspiration, which prevents broader use of office-based surgery in the nose. As such, there exists a long felt but unmet need to provide a device that will seal off the remainder of the upper airway and expand access to office-based nasal and sinus surgeries and other procedures that would offer financial and accessibility advantages over conventional sinus surgery.

There are devices intended to stop nose bleeding or epistaxis. These include a variety of forms of nasal packing, and may be referred to as nasal tampons or intranasal balloons. However, they tend to share the same concept of applying pressure to the site of the bleeding to control the bleeding. Devices to control intranasal bleeding generally are of two major types, based on their positioning during use, and they include anterior and posterior devices. Existing anterior devices generally would not permit access to intranasal surgery. Posterior devices to date have been designed to be placed in a patient who has nasal bleeding that cannot otherwise be controlled by putting pressure on the sphenopalatine artery, which is the major source of blood supply to the posterior portion of the nose. Moreover, the anatomic location in which posterior epistaxis balloons are placed would not be useful during office-based sinus surgery, due to the volume of such devices and the lack of a suction system, which would result in blood quickly obscuring the field. Thus, there remains a need for a device that will facilitate less expensive and more convenient office-based nasal and sinus surgeries and other procedures.

SUMMARY

In a first aspect, the disclosure provides an intranasal expandable occlusion device that includes an expandable body. The expandable body further includes a flexible and inflatable balloon that is surrounded by at least one flexible and expandable sponge having an exterior surface, and a flexible and expandable cover that is impermeable to liquids and overlies a portion of the exterior surface of the at least one sponge but that includes access to the at least one sponge proximate an anterior end of the at least one sponge. The device also includes an inflation catheter connected to the balloon and a suction catheter connected to the sponge.

In a second aspect, the disclosure provides a method of providing intranasal occlusion for a patient including the steps of: obtaining an intranasal expandable occlusion device wherein the device has an expandable body and further includes a flexible and inflatable balloon that is surrounded by at least one flexible and expandable sponge having an exterior surface, and a flexible and expandable cover that is impermeable to liquids and overlies a portion of the exterior surface of the at least one sponge but that includes access to the at least one sponge proximate an anterior end of the at least one sponge, an inflation catheter connected to the balloon, and a suction catheter connected to the sponge; inserting the body of the intranasal expandable occlusion device into the nose of the patient in an unexpanded condition; positioning the body of the intranasal expandable occlusion device in the choanae and nasopharnyx; and expanding the body of the intranasal expandable occlusion device so as to seal the choanae and nasopharynx.

In contrast to prior art devices, the device of this disclosure is not designed to simply stop internal nasal bleeding by applying pressure on the major arteries in the posterior nose. Instead, it is designed to be relatively compact yet seal off the posterior nasal cavity from the rest of the upper airway and to suction fluid, such as blood or other fluids from the nose during a surgical procedure. More specifically, the device is designed to occlude the choanae in the posterior nasal cavity to prevent fluid, such as blood, medications or other fluids from draining into the airway during surgery and to remove the fluid from the field. In addition, the materials, sizing and shapes used are designed to make the device comfortable enough to be used during office-based surgery, while being secure enough to seal off the nasal cavity from the upper airway, to prevent aspiration.

Thus, the device is advantageously designed to eliminate the need for general anesthesia for nasal and sinus surgeries. It also is designed to be low-profile, such that the body of the device rests in the nasopharynx with the anterior extent occluding the choanae bilaterally, and permitting working space within the nasal cavity for endoscopic nasal and sinus surgeries, and other procedures. The inclusion of a flexible and inflatable balloon surrounded by the at least one flexible and expandable sponge enhances comfort and adaptability to different patient anatomy of the choanae and nasopharynx, while using a flexible and expandable cover that is impermeable to liquids and overlies a portion of the at least one sponge creates a seal to prevent drainage from the nasal cavity into the rest of the upper airway. The bilateral design effectively provides two anterior faces designed to occlude the two respective choanae. The inclusion of a flexible expandable cover over a portion of the at least one sponge and providing access to the at least one sponge proximate an anterior end of the at least one sponge also allows fluid, such as blood or other fluids to drain into the sponge of the body, so that it can be suctioned out via the suction catheter, without allowing fluid to exit the posterior of the at least one sponge and flow into the upper airway.

Thus, the device is not designed to control nasal hemorrhage by exerting pressure on the site of bleeding, but rather is designed to seal off the nasal cavity from the rest of the upper airway, while also providing generous working space in the nasal cavity and simultaneously collecting and evacuating fluid, such as blood and other fluids to facilitate an unobstructed field for nasal and sinus surgical procedures.

It will be appreciated that the device may permit a variety of surgical and other procedures to be performed in an office-based setting that includes a suction source. It is contemplated that such procedures may include, for example, minor revision sinus surgery, "Mini-Fess" or endoscopic sinus surgery in which there is minimal dissection, inferior turbinate reduction, rhinoplasty, and septoplasty, and repair of nasal septal perforation. Additional applications also are contemplated, including, for example, use during office-based cauterization of epistaxis, biopsy of nasal masses and debridement of sinus cavity in a patient with a bleeding disorder, delivery of intranasal medications and intranasal irrigation. It will further be appreciated that some or all of these types of procedures may be facilitated by use of this new device and the device is not limited to these uses, but may find uses in still further procedures.

As above noted, the example intranasal expandable occlusion device and example methods of using the same of this disclosure provide several advantageous features. It also is to be understood that both the foregoing general description and the following detailed description are exemplary and provided for purposes of explanation only, and are not restrictive of the claimed subject matter. Further features and objects of the present disclosure will become more fully apparent in the following description of the preferred embodiments and from the appended claims.

BRIEF DESCRIPTION OF THE DRAWINGS

In describing the preferred embodiments, reference is made to the accompanying drawing figures wherein like parts have like reference numerals, and wherein.

It should be understood that the drawings are not to scale. While some mechanical details of example intranasal expandable occlusion devices, including other plan and section views of the example shown, and of examples that may have alternative configurations, have not been included, such details are considered within the comprehension of those of skill in the art in light of the present disclosure. It also should be understood that the present invention is not limited to the example embodiments illustrated.

BRIEF DESCRIPTION OF THE PREFERRED EMBODIMENT

Figure 1:
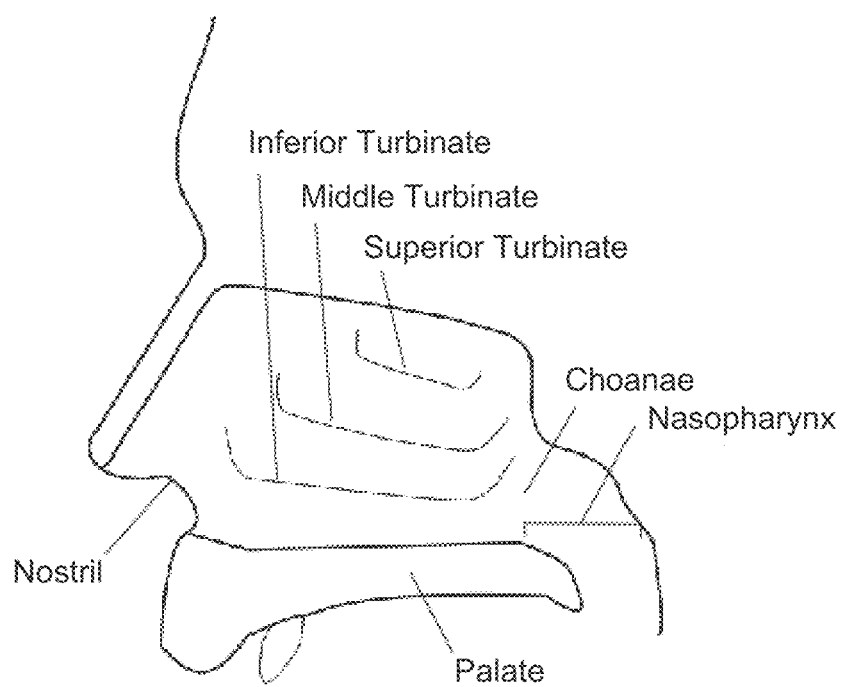
FIG. 1 is a schematic view that illustrates the relevant anatomy of the posterior nasal cavity and nasopharynx of a patient.

The general relevant anatomy of the posterior nasal cavity and nasopharynx of a patient are shown in FIG. 1. Thus, the nostrils present anterior nares and a nasal cavity includes the inferior turbinate, the middle turbinate and the superior turbinate, which are above the palate and anterior to the choanae and nasopharynx. This sets the stage for the area within which nasal and sinus surgeries and other procedures often are performed. Unfortunately, this also is a crowded space within which a surgeon must operate and which has a tendency to generate bleeding that can obscure the field or site of the surgical procedure.

Figure 2:
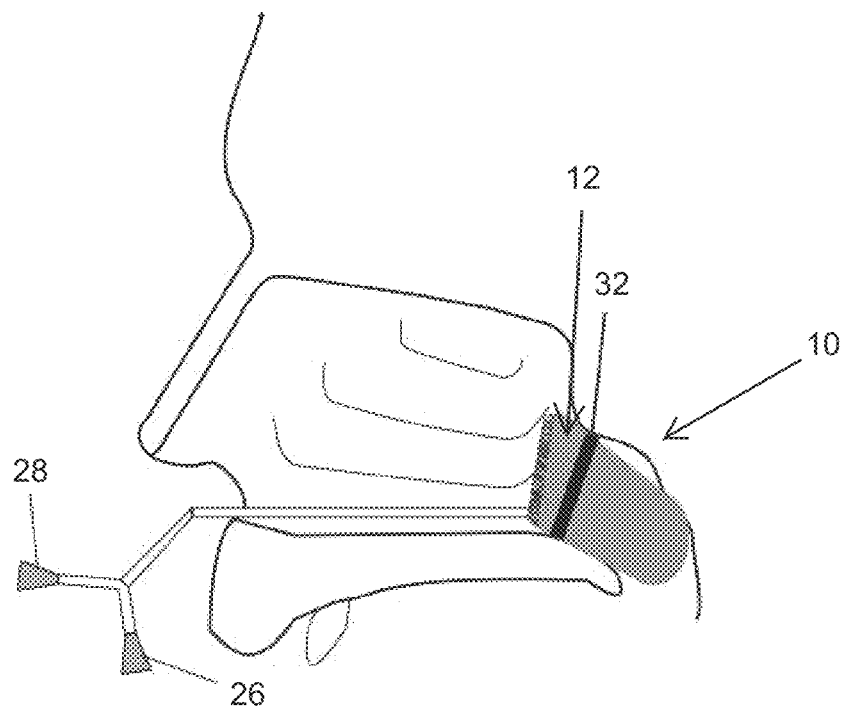
FIG. 2 is a schematic view that illustrates an example intranasal expandable occlusion device of the present disclosure positioned in the posterior nose.

FIGS. 2-7 provide an example intranasal expandable occlusion device 10, which is shown in FIG. 2 in a preferred location for use within the relevant anatomy of the posterior nasal cavity and nasopharynx, so as to seal off the rest of the upper airway and prevent aspiration. As may be seen in FIG. 3, the device 10 includes an expandable body 12. The body 12 further includes a flexible inflatable balloon 14 that is surrounded by at least one flexible expandable sponge 16 having an exterior surface 18, and a flexible expandable cover 20 that is impermeable to liquids and overlies a portion of the exterior surface 18 of the at least one sponge 16 but that includes access to the at least one sponge 16 proximate an anterior end 24 of the at least one sponge 16. In this example, the cover 20 extends over the posterior end and along the sides of the at least one sponge 16, and access to the at least one sponge 16 is provided by an opening 22 toward an anterior end of the at least one sponge 16. The opening 22 will allow fluid, such as blood and other fluids to reach and be collected by the at least one sponge 16. The device 10 also includes an inflation catheter 26 connected to the balloon 14, and a suction catheter 28 connected to the sponge 16.

The at least one sponge 16 of the intranasal expandable occlusion device 10 may be of unitary construction, while being shaped for advantageous bilateral placement, or alternatively may include two or more sponges that surround the balloon 14. In a preferred embodiment, the at least one sponge 16 may be constructed as at least one poly-vinyl alcohol sponge. It will be appreciated that when the sponge 16 is constructed as a poly-vinyl alcohol sponge, or of other suitable materials, it may be expanded by applying fluid, such as by applying approximately 1 cc or more of saline to moisten the sponge. This provides a safe, effective, low pressure and cost efficient means of employing a first expansion capability of the body 12. In some instances, this may provide sufficient expansion to seal the choanae and nasopharynx. However, the intranasal expandable occlusion device 10 may be expanded to a further extent by inflating the balloon 14 that is surrounded by the sponge 16. A sealing fit within the choanae and nasopharynx may be achieved with the body 12 being of several configurations, but a particularly suitable configuration may be a construction wherein the body 12 is generally cube-shaped when expanded. Thus, for example, for an average adult patient, it may be suitable to have the body 12 dimensioned so as to have an unexpanded size that is approximately 11 mm high, 5 mm wide and 22 mm long, and an expanded size that is approximately 20 mm high, 27 mm wide and 26 mm long. It will be appreciated, however, that other dimensions may be suitable, depending on the anatomy of the patient.

The flexible expandable cover 20 is impermeable to fluids and may be constructed of a thin flexible elastomeric material, such as a sheet or film of elastomeric plastic, rubber or other suitable elastomeric material that accommodates expansion of the sponge 16 and/or balloon 14. The device 10 is shown in an unexpanded condition in FIG. 4, and in an expanded condition in FIGS. 5 and 6. The cover 20 has an outer surface 30. As best seen in FIGS. 2 and 4-6, the outer surface 30 of the cover may feature a line 32 that corresponds to a preselected desired positioning of the body 10 when in use in a patient, and the cover 20 permits fluid to be collected in the sponge 16 without passing through the least one sponge 16 to the upper airway.

Figure 3:
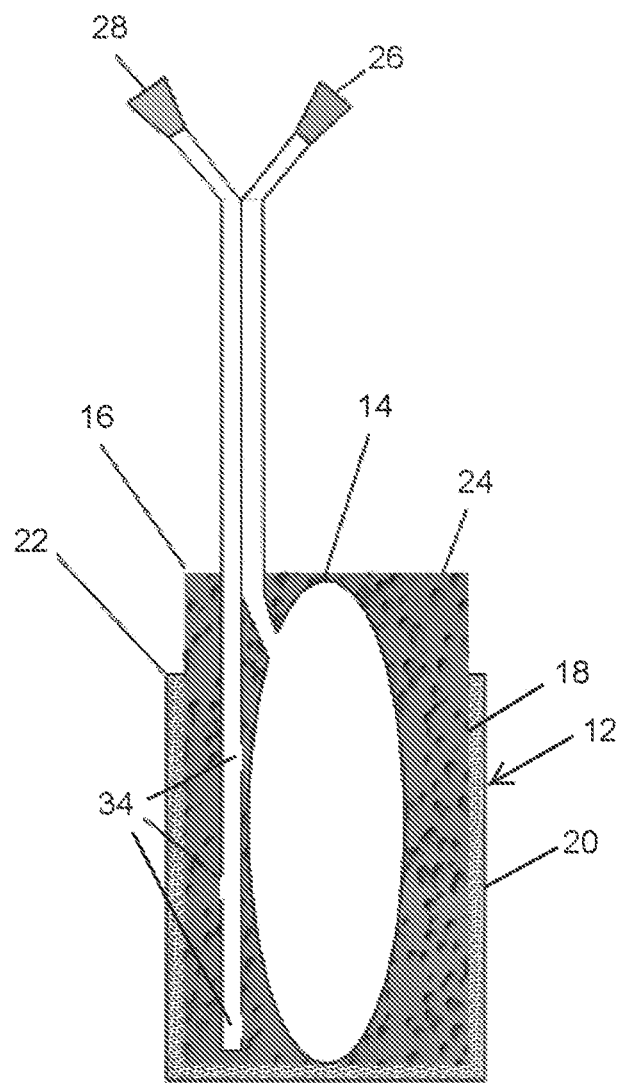
FIG. 3 is a schematic cross-section view that illustrates the components of the device shown in FIG. 2.
Figure 4:
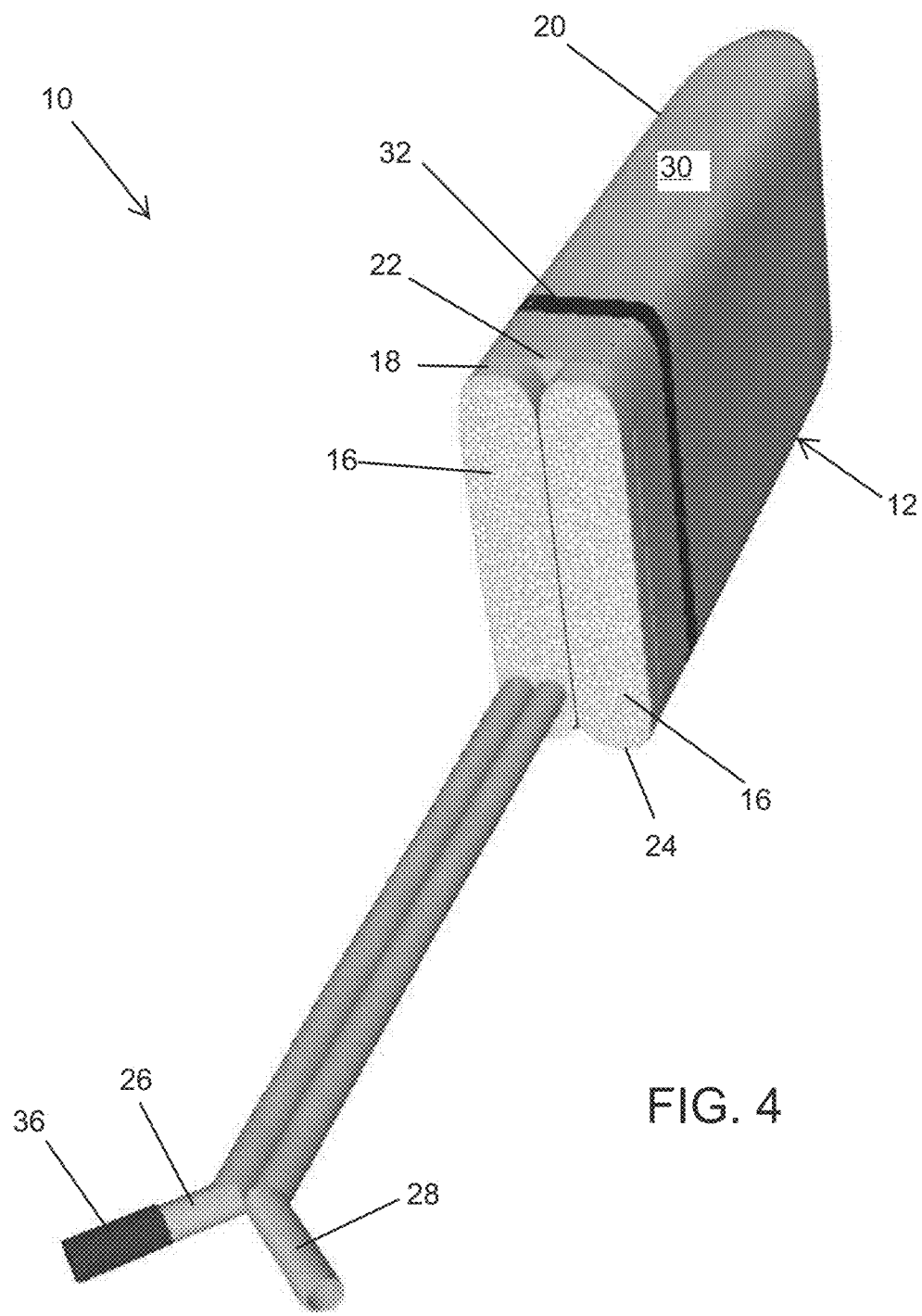
FIG. 4 is a schematic anterior perspective view that illustrates the device shown in FIG. 2 in an unexpanded condition.
Figure 5:
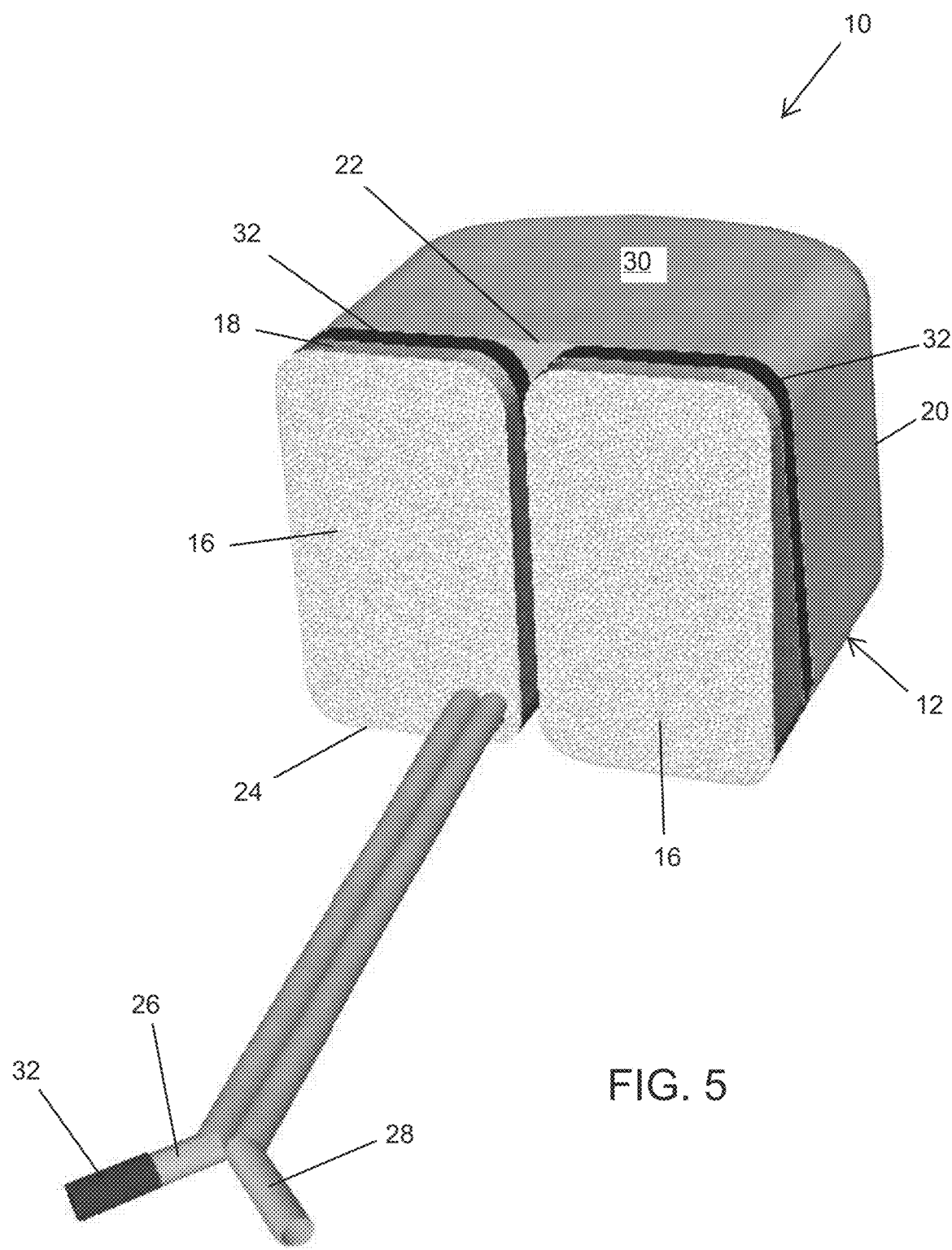
FIG. 5 is a schematic anterior perspective view that illustrates the device shown in FIG. 2 in an expanded condition.
Figure 6:
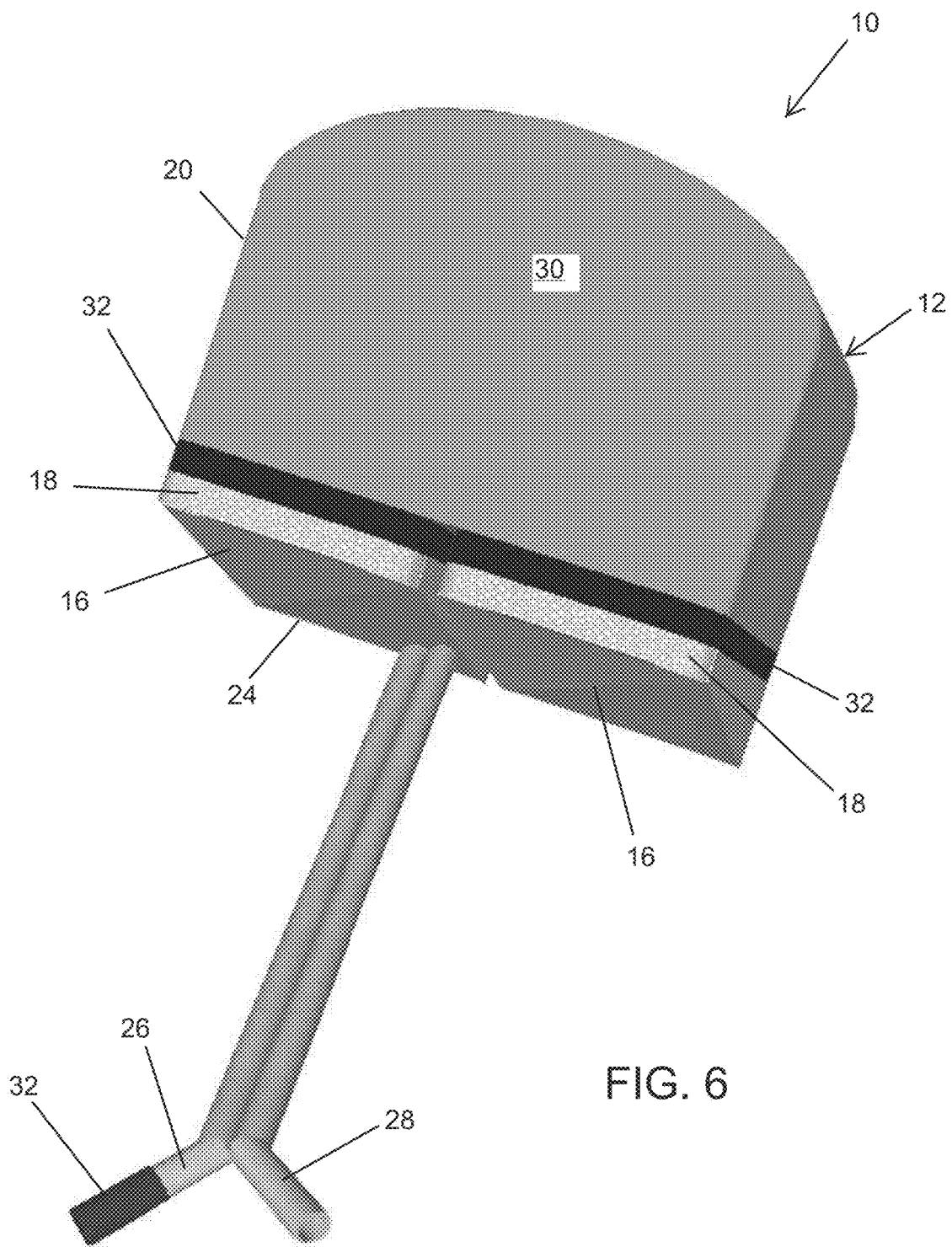
FIG. 6 is a schematic upper perspective view that illustrates the device shown in FIG. 2 in the expanded condition shown in FIG. 5.
Figure 7:
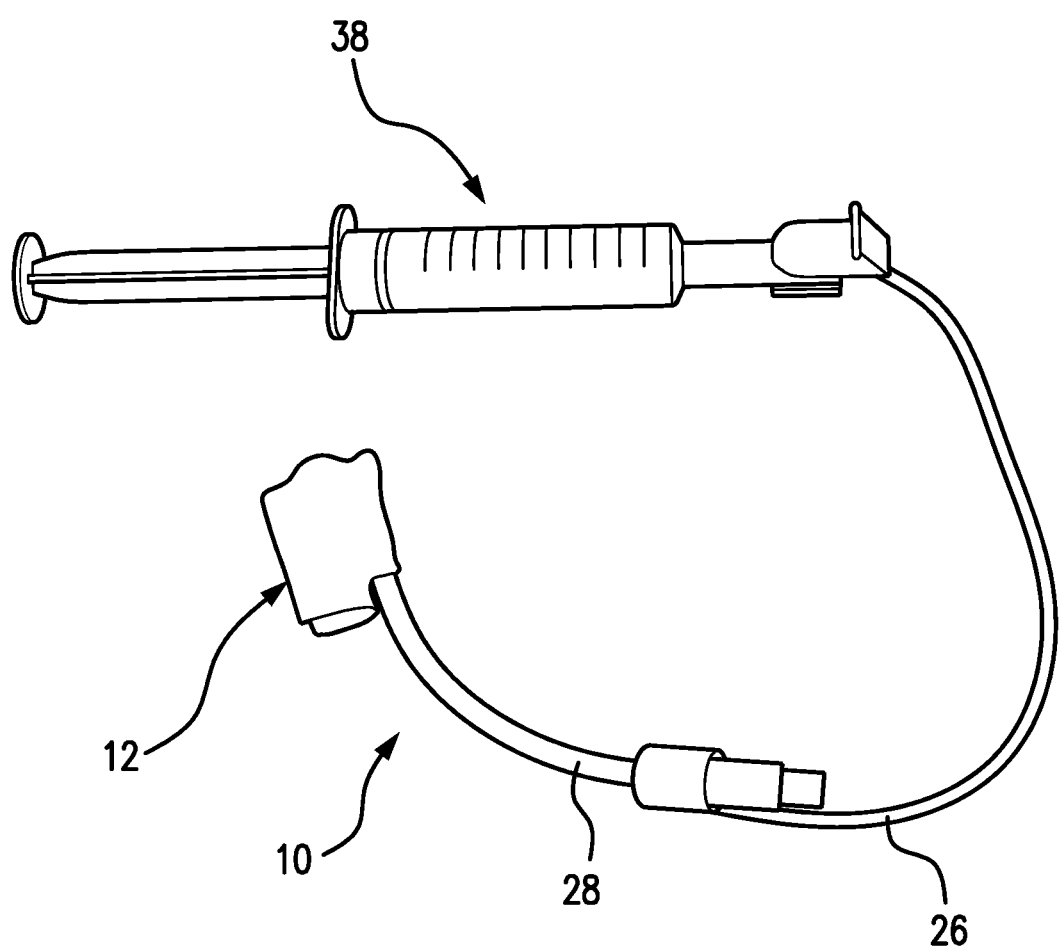
FIG. 7 is a perspective view of the device shown in FIG. 2 and further connected to a source for inflation of the balloon.

As best seen in FIG. 3, the suction catheter 28 of the intranasal expandable occlusion device 10 includes a plurality of openings 34 that are located within the at least one sponge 16. In addition, the inflation catheter 26 that is connected to the balloon 14 may be connected at its proximal end to a suitable inflation source 38, which is shown in FIG. 7 as a syringe. The inflation catheter 26 preferably includes a one way valve 36 or other suitable configuration at its proximal end, to ensure that the balloon will not inadvertently collapse during a procedure. Depending on the characteristics of the balloon 14, the inflation source 38 may provide fluid for inflation of the balloon 14 that could range from a gas to a liquid, and may be other than a syringe.

The present disclosure also provides a method of providing intranasal occlusion for a patient comprising multiple steps. The steps include locating an intranasal expandable occlusion device 10 that includes an expandable body 12 further having a flexible inflatable balloon 14 that is surrounded by at least one flexible expandable sponge 16 having an exterior surface 18, and a flexible expandable cover 20 that is impermeable to fluids and overlies a portion of the exterior surface 18 of the at least one sponge 16 but that includes access to the at least one sponge 16 proximate an anterior end 24 of the at least one sponge 16. The access in this example is provided by an opening 22 near the anterior end of the at least one sponge 16. The device 10 also includes an inflation catheter 26 connected to the balloon 14 and a suction catheter 28 connected to the sponge 16. The method further includes the steps of inserting the body 12 of the intranasal expandable occlusion device 10 into the nose of the patient in an unexpanded condition, such as the condition shown in FIG. 4, and positioning the body 12 of the intranasal expandable occlusion device in the choanae and nasopharynx. The method additionally includes the step of expanding the body 12 of the device 10 so as to seal the choanae and nasopharynx, as may be seen in FIG. 2.

The step of inserting the body 12 of the intranasal expandable occlusion device may further include inserting the body 12 via anterior nares of the patient under endoscopic guidance. As noted above, the cover 20 may further include an outer surface 30 having a line 32 that corresponds to a preselected desired positioning of the body when in use, and the method may include using the line 32 for preferred placement when positioning the body 12 of the device 10 in the choanae.

The method also may include wherein the at least one sponge 16 further includes two or more sponges that surround the balloon 14 and/or the at least one sponge 16 further includes at least one poly-vinyl alcohol sponge, or at least one sponge constructed of other suitable materials. It will be appreciated that the step of expanding the body 12 may include moistening the at least one sponge 16, and further may include inflating the balloon 14 via the inflation catheter 26. The body 12 also may be further expanded simply by including a step of inflating the balloon 14.

After inserting the intranasal expandable occlusion device 10, the step of positioning the body 12 of the device 10 in the choanae and nasopharynx may include adjusting the position for patient comfort. Ideally, the device 10 may be used without need for general anesthesia, and therefore, without need to be within a full hospital operating room.

The method of providing intranasal occlusion for a patient also may include using the suction catheter 28 to remove fluids that have been collected within the at least one sponge 16. The method also may include steps associated with additional equipment, such as additional air inflation or suction systems or medication delivery systems to perform other procedures, such as delivery of intranasal medications or intranasal irrigation. It further will be appreciated that upon completion of a procedure wherein the device 10 is used, the body 12 may be removed with the balloon 14 in a deflated condition by pulling the body 12 anteriorly through the nose of the patient.

The disclosed intranasal expandable occlusion device provides a novel and highly advantageous option for use with patients that may undergo surgery or other procedures within a physician's office or another cost effective setting. The device provides for appropriate space for surgery or other procedures, while sealing off the rest of the upper airway, to prevent aspiration. While the disclosed device is susceptible of embodiment in many different forms, there is shown in the drawings an example embodiment with the understanding that the present disclosure can be considered as an exemplification of the principals of the invention and is not intended to limit the invention to the example embodiment illustrated, and is only limited by the appended claims and legal equivalents thereof.

The invention claimed is:

1. An intranasal expandable occlusion device, comprising:
    an expandable body having a first end and an opposite, second end, and comprising:
        at least one flexible expandable sponge having an anterior end, an opposite, posterior end and an exterior surface defined therebetween;
        a flexible inflatable balloon that is completely surrounded by and is completely in contact with the at least one flexible expandable sponge so that no portion of the flexible inflatable balloon is uncovered by the at least one flexible expandable sponge; and
        a flexible expandable cover that is impermeable to liquids and overlies a portion of the exterior surface of the at least one expandable sponge and extends over the posterior end and along sides of the at least one expandable sponge so as to define an uncovered portion including the anterior end and a portion proximate the anterior end of the at least one expandable sponge uncovered by the flexible expandable cover that provides an access to the at least one expandable sponge, wherein the access is an opening that allows fluid to reach and be collected by the at least one expandable sponge;
        wherein the first end and the second end of the expandable body are respectively coincident with the anterior end and the posterior end of the at least one flexible expandable sponge, and the expandable body has no through passageway extending from the posterior end to the anterior end of the at least one flexible expandable sponge such that when the expandable body rests in an airway of a structure in use, the expandable body operably occludes the airway bilaterally for preventing drainage from passing through the expandable body;

an inflation catheter connected to the flexible inflatable balloon through the uncovered portion of the at least one expandable sponge; and a suction catheter connected to the at least one expandable sponge through the uncovered portion of the at least one expandable sponge, for suctioning the fluid collected by the at least one expandable sponge.

2. The intranasal expandable occlusion device of claim 1, wherein the at least one expandable sponge comprises two sponges that surround the flexible inflatable balloon.

3. The intranasal expandable occlusion device of claim 1, wherein the at least one expandable sponge is formed of poly-vinyl alcohol.

4. The intranasal expandable occlusion device of claim 1, wherein the at least one expandable sponge is expandable by applying fluid to moisten the at least one expandable sponge.

5. The intranasal expandable occlusion device of claim 1, wherein the at least one expandable sponge is expandable by inflating the flexible inflatable balloon.

6. The intranasal expandable occlusion device of claim 1, wherein the expandable body is generally cube-shaped when expanded.

7. The intranasal expandable occlusion device of claim 1, wherein the expandable body is dimensioned to have an expanded size that is approximately 20 mm high, 27 mm wide and 26 mm long.

8. The intranasal expandable occlusion device of claim 1, wherein the flexible expandable cover comprises an outer surface having a line that corresponds to a preselected desired positioning of the expandable body when in use.

9. The intranasal expandable occlusion device of claim 1, wherein the flexible expandable cover is formed of an elastomeric material.

10. The intranasal expandable occlusion device of claim 1, wherein the suction catheter includes a plurality of openings that are located within the at least one expandable sponge.

11. A method of providing intranasal occlusion for a patient, comprising the steps of:

providing an intranasal expandable occlusion device comprising an expandable body having a first end and an opposite, second end, and comprising:

at least one flexible expandable sponge having an anterior end, an opposite, posterior end and an exterior surface defined therebetween;

a flexible inflatable balloon that is completely surrounded by and is completely in contact with the at least one flexible expandable sponge so that no portion of the flexible inflatable balloon is uncovered by the at least one flexible expandable sponge; and a flexible expandable cover that is impermeable to liquids and overlies a portion of the exterior surface of the at least one expandable sponge and extends over the posterior end and along sides of the at least one expandable sponge so as to define an uncovered portion including the anterior end and a portion proximate the anterior end of the at least one expandable sponge uncovered by the flexible expandable cover that provides an access to the at least one expandable sponge, wherein the access is an opening that allows fluid to reach and be collected by the at least one expandable sponge;

wherein the first end and the second end of the expandable body are respectively coincident with the anterior end and the posterior end of the at least one flexible expandable sponge, and the expandable body has no through passageway extending from the posterior end to the anterior end of the at least one flexible expandable sponge such that when the expandable body rests in an airway of a structure in use, the expandable body operably occludes the airway bilaterally for preventing drainage from passing through the expandable body;

an inflation catheter connected to the flexible inflatable balloon through the uncovered portion of the at least one expandable sponge; and a suction catheter connected to the at least one expandable sponge through the uncovered portion of the at least one expandable sponge, for suctioning the fluid collected by the at least one expandable sponge;

inserting the expandable body of the intranasal expandable occlusion device into the nose of the patient in an unexpanded condition;

positioning the expandable body of the intranasal expandable occlusion device in an airway of a nasal structure including the choanae and nasopharnyx adjacent a nasal cavity; and expanding the expandable body of the intranasal expandable occlusion device so as to seal off the nasal cavity from the airway, thereby occluding the airway bilaterally for preventing drainage from the nasal cavity into the airway.

12. The method of claim 11, wherein the step of inserting the expandable body of the intranasal expandable occlusion device further comprises inserting the expandable body via anterior nares of the patient under endoscopic guidance.

13. The method of claim 11, wherein the flexible expandable cover comprises an outer surface having a line that corresponds to a preselected desired positioning of the expandable body when in use and the line is used for preferred placement when positioning the expandable body of the intranasal expandable occlusion device in the choanae.

14. The method of claim 11, wherein the at least one expandable sponge is formed of poly-vinyl alcohol.

15. The method of claim 11, wherein the step of expanding the expandable body further comprises moistening the at least one expandable sponge.

16. The method of claim 11, wherein the step of expanding the expandable body further comprises inflating the flexible inflatable balloon via the inflation catheter.

17. The method of claim 11, wherein the step of positioning the expandable body of the intranasal expandable occlusion device in the choanae and nasopharynx includes adjusting the position for patient comfort.

18. The method of claim 11, further comprising using the suction catheter to remove fluid from within the at least one expandable sponge.

19. The method of claim 11, wherein upon completion of a procedure, the expandable body is removed with the flexible inflatable balloon in a deflated condition by pulling the expandable body anteriorly through the nose.

20. The method of claim 11, further comprising a step of delivering intranasal medication or intranasal irrigation.

* * * * *